United States Patent [19]

Hauck et al.

[11] 4,127,717
[45] Nov. 28, 1978

[54] BENZO-CYCLITOLAMINES

[75] Inventors: Frederic P. Hauck, Bridgewater; Joyce Reid, Dayton, both of N.J.

[73] Assignee: E. R. Squibb & Sons, Inc., Princeton, N.J.

[21] Appl. No.: 888,128

[22] Filed: Mar. 20, 1978

[51] Int. Cl.² ........................................ C07D 295/10
[52] U.S. Cl. ................................... 544/154; 544/155; 544/380; 560/252; 260/326.33; 546/204; 546/203; 546/184
[58] Field of Search ...................... 544/154, 155, 380; 560/252; 260/326.33, 293.62

[56] References Cited

U.S. PATENT DOCUMENTS

| 3,894,031 | 7/1975 | Hauck et al. | 260/293.56 |
|---|---|---|---|
| 3,971,823 | 7/1976 | Hauck et al. | 260/490 |
| 3,984,419 | 10/1976 | Hauck et al. | 260/326.33 |
| 4,065,485 | 12/1977 | Hauck et al. | 260/464 |

OTHER PUBLICATIONS

Fokin et al., "Chem Abstracts", vol. 72 (1970) No. 90132h.
Jones et al., "Chem Abstracts", vol. 74 (1971) No. 40985j.

Primary Examiner—Henry R. Jiles
Assistant Examiner—R. W. Ramsuer
Attorney, Agent, or Firm—Lawrence S. Levinson; Merle J. Smith; Donald J. Barrack

[57] ABSTRACT

Compounds having the formula

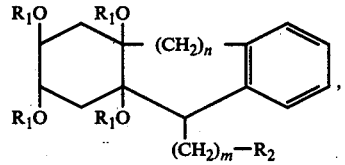

and the pharmaceutically acceptable salts thereof, wherein $n$ is 1 or 2; $m$ is 2, 3 or 4; $R_1$ is alkanoyl; and $R_2$ is a tertiary amino group; have hypotensive activity.

10 Claims, No Drawings

BENZO-CYCLITOLAMINES

BACKGROUND OF THE INVENTION

Various cyclitol derivatives are disclosed in the prior art as having hypotensive activity. United States patent 3,894,301, issued July 8, 1975, discloses, inter alia, compounds having the formula

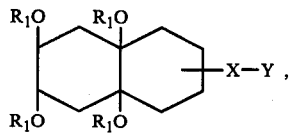

wherein $R_1$ is as defined hereinafter, X is a bivalent aliphatic radical and Y is an amino group, certain substituted amino groups, or certain nitrogen containing heterocyclic groups. Compounds having the above formula wherein Y represents certain substituted amino groups not disclosed in the above referenced patent are disclosed in United States patents 3,971,823, issued July 27, 1976 and 4,065,485 issued Dec. 27, 1977.

SUMMARY OF THE INVENTION

Compounds having the formula

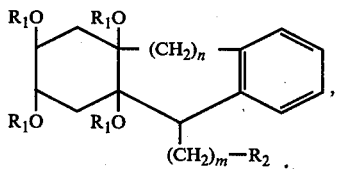

and the pharmaceutically acceptable salts thereof, have useful hypotensive activity. In formula I, and throughout the specification, the symbols are as defined below.

$R_1$ is alkanoyl;

$R_2$ is dialkylamino, 1-pyrrolidinyl, 1-piperidinyl, 4-alkyl-1-piperazinyl or 4-morpholinyl;

$n$ is 1 or 2; and $m$ is 2, 3 or 4.

The term "alkanoyl", as used throughout the specification, refers to groups having 2 to 7 carbon atoms.

The term "alkyl", as used throughout the specification, refers to groups having 1 to 6 carbon atoms.

DETAILED DESCRIPTION OF THE INVENTION

The compounds of formula I can be prepared utilizing as a starting material a compound having the formula

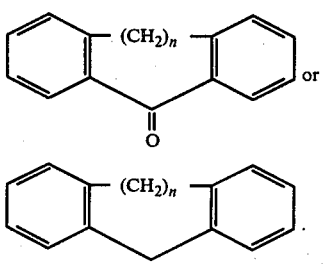

Reaction of a compound of formula II with a Grignard reagent having the formula $$R_2-(CH_2)_m-MgX, \quad (IV)$$

wherein X is a halogen atom, yields an intermediate having the formula

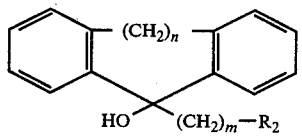

The reaction can be run in an organic solvent such as tetrahydrofuran, at the reflux temperature of the solvent. Conveniently, the Grignard reagent of formula IV can be formed in situ by mixing magnesium and an aminoalkylhalide having the formula $$R_2-(CH_2)_m-X \quad (VI)$$

wherein X is a halogen atom. In some instances it may be necessary to add a dihaloalkylene compound to initiate the reaction.

Reaction of a compound of formula III with a compound of formula IV yields an intermediate having the formula

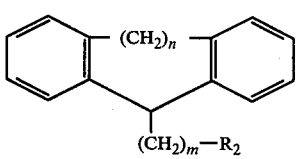

The reaction is run in the presence of a proton removing agent such as sodium amide and can be run in a mixture of an organic solvent, e.g., ether, and liquid ammonia.

When an intermediate of either formula V or VII is subjected to a Birch reduction, the resultant diene intermediate will have the formula

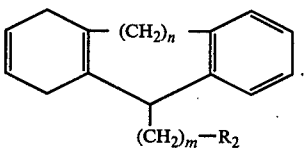

The well-known Birch reduction comprises the reduction of an aromatic compound using ammonia and a metal. For the reduction of an aromatic compound of formula V or VII it has been found effective to utilize lithium ribbon as the metal.

Oxidation of a diene intermediate of formula VIII yields a tetrol derivative having the formula

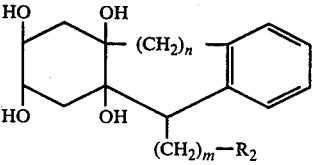

The oxidation can be accomplished by treating a diene of formula VIII with formic acid and hydrogen peroxide followed by basic hydrolysis. The tetrols of formula IX are novel intermediates, and as such, they constitute an integral part of this invention.

A tetrol intermediate of formula IX can be converted into the corresponding product of formula I by reaction with the appropriate acid anhydride (($R_1CO)_2O$) in the presence of an acid catalyst such as perchloric acid.

The compounds of formula I contain five asymmetric centers; i.e., the four carbon atoms to which are attached the $R_1O$— groups and the carbon atom to which is attached the $R_2$—$(CH_2)_m$— group. In the preferred embodiment of this invention, the $R_1O$— groups are axially oriented and the fusion of the two aliphatic rings is, therefore, trans. The $R_2$—$(CH_2)_m$— group can be oriented either cis or trans to the closest $R_1O$— group. The compounds exist as racemic mixtures and can be separated into their optical isomers using conventional techniques.

The compounds of formula I are useful for the treatment of hypertension in mammals. For this purpose, they can be administered in daily doses of from 5 to 50 milligrams per kilogram of body weight; preferably about 5 to 25 milligrams per kilogram of body weight can be administered in single or divided doses.

The compounds of the present invention can be administered orally, for example, with an inert diluent or with an assimilable edible carrier, or they can be enclosed in hard or soft gelatin capsules, or they can be compressed into tablets, or they can be incorporated directly with the food of the diet. For oral therapeutic administration, the active compounds of this invention can be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations can, of course, be varied and can conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The following examples are specific embodiments of this invention.

EXAMPLE 1

2,3:4a,11a-trans-5-[3-(Dimethylamino)propyl]-1,2,3,4,10,11-hexahydro-5H-dibenzo[a,d]cycloheptene-2,3,4a,11a-tetrol, tetraacetate ester (A)
5-[3-(Dimethylamino)propyl]-10,11-dihydro-5H-dibenzo[a,d]cyclohepten-5-ol 3-(Dimethylamino)propyl chloride (110 g) is dissolved in 600 ml of tetrahydrofuran. About 10% of this solution is added to the reaction flask containing 26.4 g of magnesium and 50 ml of tetrahydrofuran. The mixture is heated to reflux and reaction is initiated with ethylene dibromide. The remaining halide is added slowly (over about 30 minutes) to control the rate of reflux. The mixture is then heated under reflux for an additional 30 minutes. After cooling in an ice bath, 100 g of dibenzosuberone in 200 ml of tetrahydrofuran is added slowly (over about 30 minutes). The mixture is heated under reflux for 1.5 hours. After cooling in an ice bath, the mixture is decomposed by dropwise addition of saturated ammonium chloride solution (1 liter added in 2 hours). The mixture is stirred for an additional hour, the layers are separated and the aqueous layer is reextracted with ether. The combined organic layers are dried over magnesium sulfate, filtered and the solvent is removed in vacuo. The residue is dissolved in ether and extracted with 10% hydrochloric acid. The aqueous layer is basified with sodium hydroxide and extracted twice with ether. The ether extracts are dried, filtered, and the solvent is removed in vacuo leaving 103 g of a solid.

(B)
4,5,10,11-Tetrahydro-N,N-dimethyl-1H-dibenzo[a,d]cycloheptene-5-propanamine

5-[3-(Dimethylamino)propyl]-10,11-dihydro-5H-dibenzo[a,d]cyclohepten-5-ol (50.2 g) is partially dissolved in 350 ml of ether and added to 2 liters of liquid ammonia. Lithium ribbon (4.73 g) is then added portionwise over a period of 15 minutes. After stirring for 20 minutes, absolute alcohol is added dropwise until the color is discharged (about 90 ml added over a period of 1 hour). More ether is added and the ammonia is boiled off. While cooling in an ice bath the mixture is diluted slowly with 1 liter of water. The layers are separated and the aqueous layer is reextracted with ether. The combined organic layers are dried over potassium carbonate, filtered, and the solvent is removed in vacuo, leaving 47.0 g of an oil. NMR indicates this is about 50% of the desired diene (the bulk of remaining material being unreduced starting material).

(C)
2,3:4a,11a-trans-5-[3-(Dimethylamino)propyl]-2,3,4,5,10,11-hexahydrodibenzo[a,d]cycloheptene-2,3,4a,11a-tetrol Crude 4,5,10,11-tetrahydro-N,N-dimethyl-1H-dibenzo[a,d]cycloheptene-5-propanamine (47 g) is added slowly to 200 ml of cold 88% formic acid. Hydrogen peroxide (80 ml of 30%) is added dropwise over a period of 30 minutes at a temperature below 35° C. After addition is complete, the temperature is allowed to rise to 50° C. and held at 40°–50° C. for 1 hour before the mixture is left stirring for about 16 hours in a water bath at room temperature. The mixture is taken to near dryness in vacuo. Water is added twice and removed in vacuo (negative to starch-potassium iodide paper after second addition). The viscous residue is dissolved in 200 ml of ethanol, cooled in an ice bath and treated with a solution of 70 g of potassium hydroxide in 80 ml of water. After heating for 30 minutes on a steam bath, the mixture is diluted to about 600 ml with ice water. Four ether extractions yield 47.8 g of viscous material which fails to crystallize. This is chromatographed on 1 kg of Activity IV basic alumina. The tetrol product is eluted with chloroform and 2% methanol in chloroform. Fractions weighing 12.8 g are primarily the contaminated tetrol. The material fails to crystallize.

(D)
2,3:4a,11a-trans-5-[3-(Dimethylamino)propyl]-1,2,3,4,10,11-hexahydro-5H-dibenzo[a,d]cycloheptene-2,3,4a,11atetrol, tetraacetate ester 2,3:4a,11a-trans-5-[3-(Dimethylamino)propyl]-1,2,3,4,10,11-hexahydro-5H-dibenzo[a,d]cycloheptene-2,3,4a,11a-tetrol (2.4 g) is dissolved in 25 ml of acetic anhydride and 1 ml of glacial acetic acid. The solution is cooled to −40° C. and 2 ml of 70% perchloric acid is added dropwise. The mixture is stored for about 16 hours at −12° C. After cooling to −30° C., 13 ml of methanol is added dropwise over a period of 30 minutes. The mixture is poured into 75 ml of cold concentrated ammonium hydroxide. The product is extracted into chloroform, filtered, and the solvent is removed in vacuo leaving 3.0 g of foam. Hexane is added and 1.6 g of crystalline material is deposited. This is recrystallized from ethyl acetate-hexane to give 1.17 g of the title compound, melting point 193°–197° C. (shrinking occurs at 186° C.).

Anal. Calc'd. for $C_{28}H_{39}O_8N$: C, 64.97; H, 7.60; N, 2.71. Found: C, 65.23; H, 7.81; N, 2.61.

EXAMPLE 2

2,3:4a,9a-trans-9-[3-(Dimethylamino)ethyl]-1,2,3,4,4a,9-,9a,-10-octahydro-2,3,4a,9a-anthracenetetrol, tetraacetate ester (A)

9,10-Dihydro-N,N-dimethyl-9-anthracenepropanamine

Sodium amide is prepared in 1.5 liters of liquid ammonia from 23 g of sodium and a slurry of 90.1 g (0.5M) of 9,10-dihydroanthracene in 400 ml of ether is added. A solution of 36.2 g of 3-(dimethylamino)propyl chloride in 60 ml of ether is added steadily in 3 minutes. After stirring for 1 hour, solid ammonium chloride is added in 15 minutes. More ether is added and the ammonia is boiled off. The solids are removed by filtration and washed with ether, and the filtrate is dried and taken to dryness in vacuo. The sample is redissolved in ether and the basic material is extracted into dilute hydrochloric acid. The acidic aqueous layer is washed twice with ether and basified. The product is extracted into ether, dried and freed of solvent leaving 68.2 g of the title compound.

(B)

1,4,9,10-Tetrahydro-N,N-dimethyl-9-anthracenepropanamine

A solution of 21.55 g of 9,10-dihydro-N,N-dimethyl-9-anthracenepropanamine in 100 ml of ether is added to 1 liter of liquid ammonia. Lithium ribbon (1.125 g) is added in several portions over a period of 5 minutes. After stirring for 15 minutes, absolute ethanol is added dropwise until the color is discharged (25 ml added in 30 minutes). More ether is added and the ammonia is boiled off. The mixture is then cooled in an ice bath and 500 ml of water is added. The layers are separated and the aqueous layer is reextracted with ether. The combined ether layers are dried over potassium carbonate, filtered, and the solvent is removed in vacuo leaving 21.2 g of crude product.

(C)

9-[3-(Dimethylamino)propyl]-1,2,3,4,4a,9,9a,10-octahydro-2,3,4a,9a-anthracenetetrol Crude 1,4,9,10-tetrahydro-N,N-dimethyl-9-anthracenepropanamine is added slowly to 100 ml cold 88% formic acid. Hydrogen peroxide (40 ml of 30%) is then added dropwise over a period of 1 hour maintaining the temperature below 35° C. After addition is complete, the temperature is held at 35°–45° C. for 3 hours before the mixture is left for about 64 hours in a water bath at room temperature. The mixture is taken to near dryness in vacuo. Water is added (negative to starch-potassium iodide paper) and removed in vacuo. The residue is dissolved in 100 ml of absolute ethanol and, while cooling, is treated with a solution of 36 g of potassium hydroxide in 40 ml of water. After heating on a steam bath for 30 minutes, the mixture is diluted to 300 ml with ice water. Four ether extractions give 22.6 g of viscous material which fails to crystallize and is chromatographed on 500 g of Activity IV basic alumina. Fractions eluted with 2% methanol in chloroform contains the tetrol which crystallizes on standing in ether. A total of 7.3 g of crystalline tetrol product is obtained. A 3.0 g sample was recrystallized from ethyl acetate with charcoal decolorization to give 0.9 g of the title compound, melting point 168°–176° C. (shrinking occurs at 160° C.).

(D)

2,3:4a,9a-trans-9-[3-(Dimethylamino)ethyl]-1,2,3,4,4a,9-,9a,-10-octahydro-2,3,4a,9a-anthracenetetrol, tetraacetate ester 9-[3-(Dimethylamino)propyl]-1,2,3,4,4a,9,9a,10-octahydro-2,3,4a,9a-anthracenetetrol (2.1 g) is dissolved in 25 ml of acetic anhydride and 1 ml of glacial acetic acid. The solution is cooled to −40° C. and 2 ml of 70% perchloric acid is added dropwise. The mixture is kept for about 16 hours at −12° C. After cooling to −30° C., 13 ml of methanol is added dropwise over a period of 20 minutes. The mixture is then poured into 75 ml of cold concentrated ammonium hydroxide, and immediately extracted twice with chloroform. The chloroform extracts are dried over magnesium sulfate, filtered, and the solvent is removed in vacuo leaving 2.8 g of viscous material. Hexane is added and some crystalline material is deposited. This is harvested and recrystallized from hexane-ether to give 270 mg of the title compound, melting point 168°–172° C. (shrinking occurs at 150° C.).

Anal. Calc'd. for $C_{27}H_{37}O_8N$: C, 64.39; H, 7.41; N, 2.78. Found: C, 64.42; H, 7.29; N, 2.54.

EXAMPLES 3–8

Following the procedure of Example 1, but substituting the compound listed in column I for 3-(dimethylamino)propyl chloride, yields the compound listed in column II.

| | Column I | Column II |
|---|---|---|
| 3 | 2-(dimethylamino)ethyl chloride | 2,3:4a,11a-trans-5-[2-(dimethylamino)ethyl]-1,2,3,-4,10,11-hexahydro-5$\underline{H}$-dibenzo[a,d]cycloheptene-2,3,4a,11a-tetrol, tetraacetate ester |
| 4 | 4-(diethylamino)butyl chloride | 2,3:4a,11a-trans-5-[4-(diethylamino)butyl]-1,2,3,4,-10,11-hexahydro-5$\underline{H}$-dibenzo[a,d]cycloheptene-2,3,4a,11a-tetrol, tetraacetate ester |
| 5 | 1-(2-bromoethyl)pyrrolidine | 2,3:4a,11a-trans-5-[2-(1-pyrrolidinyl)ethyl]-1,2,3,-4,10,11-hexahydro-5$\underline{H}$-dibenzo[a,d]cycloheptene-2,3,4a,11a-tetrol, tetraacetate ester |
| 6 | 1-(3-bromopropyl)piperidine | 2,3:4a,11a-trans-5-[3,-(1-piperidinyl)propyl]-1,2,3,-4,10,11-hexahydro-5$\underline{H}$-dibenzo[a,d]cycloheptene-2,3,4a,11a-tetrol, tetraacetate ester |
| 7 | 1-(4-bromobutyl)-4-methyl-piperazine | 2,3:4a,11a-trans-5-[4-(4-methyl-1-piperazinyl)butyl]-1,2,3,4,-10,11-hexahydro-5$\underline{H}$-dibenzo[a,d]cycloheptene-2,3,4a,11a-tetrol, tetraacetate ester |
| 8 | 4-(2-bromoethyl)morpholine | 2,3:4a,11a-trans-5-[2-(4-morpholinyl)ethyl]-1,2,3,4,-10,11-hexahydro-5$\underline{H}$-dibenzo- |

-continued

| Column I | Column II |
|---|---|
| | [a,d]cycloheptene-2,3,4a,11a-tetrol, tetraacetate ester |

EXAMPLES 9–15

Following the procedure of Example 2, but substituting the compound listed in column I for 3-(dimethylamino)propyl chloride, yields the compound listed in column II.

| | Column I | Column II |
|---|---|---|
| 9 | 2-(dimethylamino)ethyl chloride | 2,3:4a,9a-trans-9-(2-dimethylaminoethyl)-1,2,3,4,4a,9,9a,10-octahydro-2,3,4a,9a-anthracenetetrol, tetraacetate ester |
| 10 | 3-(di-n-hexylamino)propyl chloride | 2,3:4a,9a-trans-9-[3-(di-n-hexylamino)propyl]-1,2,3,4,4a,9,9a,-10-octahydro-2,3,4a,9a-anthracenetetrol, tetraacetate ester |
| 11 | 4-(diisopropylamino)butyl chloride | 2,3:4a,9a-trans-9-[4-(diisopropylamino)butyl]-1,2,3,4,4a,-9,9a,10-octahydro-2,3,4a,9a-anthracetetrol, tetraacetate ester |
| 12 | 1-(3-bromopropyl)pyrrolidine | 2,3:4a,9a-trans-9-[3-(1-pyrrolidinyl)propyl]-1,2,3,-4,4a,9,9a,10-octahydro-2,3,-4a,9a-anthracenetetrol, tetraacetate ester |
| 13 | 1-(4-bromobutyl)piperidine | 2,3:4a,9a-trans-9-[4-(1-piperidinyl)butyl]-1,2,3,4,-4a,9,9a,10-octahydro-2,3,4a,-9a-anthracenetetrol, tetraacetate ester |
| 14 | 2-(2-bromoethyl)-4-methylpiperazine | 2,3:4a,9a-trans-9-[2-(4-methyl-1-piperazinyl)ethyl]-1,2,3,-4,4a,9,9a,10-octahydro-2,3,4a,-9a-anthracenetetrol, tetraacetate ester |
| 15 | 4-(3-bromopropyl)morpholine | 2,3:4a,9a-trans-9-[3-(4-morpholinyl)propyl]-1,2,3,4,-4a,9,9a,10-octahydro-2,3,-4a,9a-anthracenetetrol, tetraacetate ester |

What is claimed is:

1. A compound having the formula

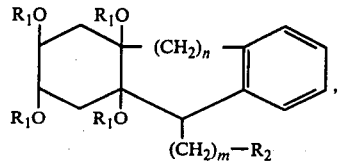

or a pharmaceutically acceptable salt thereof, wherein $R_1$ is alkanoyl having 2 to 7 carbon atoms; $R_2$ is dialkylamino, 1-pyrrolidinyl, 1-piperidinyl, 4-alkyl-1-piperazinyl, or 4-morpholinyl; $n$ is 1 or 2; and $m$ is 2, 3 or 4; wherein the term "alkyl" refers to groups having 1 to 6 carbon atoms.

2. A compound in accordance with claim 1 wherein $R_1$ is acetyl.

3. A compound in accordance with claim 2 wherein the $R_1O-$ groups are axially oriented.

4. A compound in accordance with claim 1 wherein $R_2$ is dialkylamino.

5. A compound in accordance with claim 4 wherein $R_2$ is dimethylamino.

6. A compound in accordance with claim 1 wherein $R_2$ is 1-pyrrolidinyl, 1-piperidinyl, 4-alkyl-1-piperazinyl, or 4-morpholinyl.

7. A compound in accordance with claim 1 wherein $n$ is 1.

8. A compound in accordance with claim 1 wherein $n$ is 2.

9. The compound in accordance with claim 1, 2,3:4a,11a-trans-5-[3-(dimethylamino)propyl]-1,2,3,4,10,11-hexahydro-5H-dibenzo[a,d]cycloheptene-2,3,4a,11a-tetrol, tetraacetate ester.

10. The compound in accordance with claim 1, 2,3:4a,9a-trans-9-[3-(dimethylamino)ethyl]-1,2,3,4,4a,-9,9a,10-octahydro-2,3,4a,9a-anthracenetetrol, tetraacetate ester.

* * * * *